United States Patent
Toledano et al.

(10) Patent No.: US 10,945,987 B2
(45) Date of Patent: Mar. 16, 2021

(54) METHOD FOR PROVIDING EARLY ONSET OF ACTION IN THE TREATMENT OF ROSACEA

(71) Applicant: Sol-Gel Technologies Ltd., Ness Ziona (IL)

(72) Inventors: Ofer Toledano, Kfar Saba (IL); Ofra Levy-Hacham, Ness Ziona (IL); Ori Nov, Tarum (IL); Vered Ram, Rehovot (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 0 days.

(21) Appl. No.: 16/794,734

(22) Filed: Feb. 19, 2020

(65) Prior Publication Data
US 2020/0261397 A1    Aug. 20, 2020

Related U.S. Application Data

(60) Provisional application No. 62/977,974, filed on Feb. 18, 2020, provisional application No. 62/977,952, filed on Feb. 18, 2020, provisional application No. 62/972,896, filed on Feb. 11, 2020, provisional application No. 62/972,310, filed on Feb. 10, 2020, provisional application No. 62/960,384, filed on Jan. 13, 2020, provisional application No. 62/925,258, filed on Oct. 24, 2019, provisional application No. 62/871,286, filed on Jul. 8, 2019, provisional application No. 62/871,283, filed on Jul. 8, 2019, provisional application No. 62/807,356, filed on Feb. 19, 2019, provisional application No. 62/807,368, filed on Feb. 19, 2019.

(51) Int. Cl.
| | | |
|---|---|---|
| *A61K 31/327* | (2006.01) | |
| *A61P 17/10* | (2006.01) | |
| *A61K 9/00* | (2006.01) | |
| *A61K 9/06* | (2006.01) | |
| *A61K 9/107* | (2006.01) | |
| *A61P 17/00* | (2006.01) | |
| *A61K 9/50* | (2006.01) | |
| *A61K 9/10* | (2006.01) | |

(52) U.S. Cl.
CPC .......... *A61K 31/327* (2013.01); *A61K 9/0014* (2013.01); *A61K 9/06* (2013.01); *A61K 9/10* (2013.01); *A61K 9/107* (2013.01); *A61K 9/50* (2013.01); *A61P 17/00* (2018.01); *A61P 17/10* (2018.01)

(58) Field of Classification Search
CPC .............................. A61K 31/327; A61P 17/00
USPC ......................................................... 514/714
See application file for complete search history.

(56) References Cited

U.S. PATENT DOCUMENTS

| | | | |
|---|---|---|---|
| 9,107,844 | B2 | 8/2015 | Clark et al. |
| 9,439,857 | B2 | 9/2016 | Tamarkin et al. |
| 9,687,465 | B2 | 6/2017 | Sertchook et al. |
| 9,693,988 | B2 | 7/2017 | Chang et al. |
| 2004/0171561 | A1 | 9/2004 | Popp |
| 2009/0306172 | A1 | 12/2009 | Chang et al. |
| 2010/0016443 | A1 | 1/2010 | Toledano et al. |
| 2010/0143285 | A1 | 6/2010 | Mallard et al. |
| 2011/0052515 | A1 | 3/2011 | Kaoukhov et al. |
| 2011/0262506 | A1 | 10/2011 | Toledano et al. |
| 2012/0064135 | A1 | 3/2012 | Levin et al. |
| 2013/0095185 | A1 | 4/2013 | Toledano et al. |
| 2014/0121188 | A1 | 5/2014 | Tamarkin et al. |
| 2014/0147396 | A1 | 5/2014 | Sertchook et al. |
| 2017/0216282 | A1 | 8/2017 | Dejovin et al. |
| 2017/0281571 | A1 | 10/2017 | Sertchook et al. |
| 2018/0147165 | A1 | 5/2018 | Sertchook et al. |
| 2020/0261397 | A1 | 8/2020 | Toledano et al. |

FOREIGN PATENT DOCUMENTS

| | | | |
|---|---|---|---|
| DE | 202011100767 | U1 | 12/2011 |
| WO | 2008/057411 | A1 | 5/2008 |
| WO | 2008/093346 | A2 | 8/2009 |
| WO | 2011/049547 | A1 | 4/2011 |
| WO | 2011/101868 | A2 | 8/2011 |

(Continued)

OTHER PUBLICATIONS

International Search Report and Written Opinion dated May 19, 2020 in International Patent Application No. PCT/US2020/18906, 19 pages.
Matin, et al., "Benzoyl Peroxide"; Review from StatPearls Publishing, Treasure Island (FL), 4 pages (Feb. 6, 2019).
Wepierre, et al., "Distribution and dissociation of benzoyl peroxide in cutaneous tissue after application on skin in the hairless rat", International Journal of Cosmetic Science, vol. 8, pp. 97-104 (Jun. 1986).
Nacht, et al., "Benzoyl peroxide: Percutaneous penetration and metabolic disposition", Journal the American Academy of Dermatology, vol. 4, pp. 31-37 (Jan. 1981).
International Search Report and Written Opinion dated Jul. 15, 2020 in International Patent Application No. PCT/IB2020/00125, 16 pages.

(Continued)

*Primary Examiner* — Kevin E Weddington
(74) *Attorney, Agent, or Firm* — Dentons US LLP

(57) ABSTRACT

A regimen is described for providing early onset of action in the therapeutic treatment of rosacea including topically applying a pharmaceutical composition to the skin of a subject in need of said treatment. The pharmaceutical composition includes about 1% to about 10% benzoyl peroxide as the only active ingredient, and a pharmaceutically acceptable carrier or excipient. The pharmaceutical composition is applied once daily for a period of at least about 2, 4, 8 or 12 weeks. Based on early onset of action, a primary measure of success is at least about 9%, primary measure of success being defined as a 2-grade improvement in IGA of clear or almost clear; and a secondary measure of success is at least about 40%, secondary measure of success being defined as mean inflammatory lesion count percent reduction from baseline, after at least about 2 weeks of treatment.

24 Claims, 2 Drawing Sheets

(56) References Cited

FOREIGN PATENT DOCUMENTS

WO  WO-2014083557 A1 * 6/2014 ........... A61K 31/327

OTHER PUBLICATIONS

International Search Report and Written Opinion dated Aug. 10, 2020 in International Patent Application No. PCT/IB2020/00118, 14 pages.
International Search Report and Written Opinion dated Aug. 12, 2020 in International Patent Application No. PCT/IB2020/00126, 19 pages.
International Search Report and Written Opinion dated Aug. 14, 2020 in International Patent Application No. PCT/IB2020/00123, 13 pages.
Montes, et al., "Topical Treatment of Acne Rosacea with Benzoyl Peroxide Acetone Gel," Therapeutics for the Clinician: New Reports on Treatment Modalities of Possible Interest to Patient-Caring Physicians, vol. 32, pp. 185-190 (1983).
Wilkin, et al., "Standard grading system for rosacea: Report of the National Rosacea Society Expert Committee on the Classification and Staging of Rosacea", Journal of the American Academy of Dermatology, vol. 50 (Jun. 2004), available at https://www.rosacea.org/physicians/grading-system-for-rosacea/view-online.
U.S. Non-Final Office Action dated May 28, 2020 in U.S. Appl. No. 16/794,809, 11 pages.
U.S. Non-Final Office Action dated Jul. 8, 2020 in U.S. Appl. No. 16/794,839, 9 pages.
Wollina, Uwe "Rosacea and rhinophyma in the elderly", Clinincs in Dermatology, vol. 29, pp. 61-68 (2011).
Oge, et al., "Rosacea: Diagnosis and Treatment," American Family Physician, vol. 92, pp. 187-198 (2015).
Gül, et al. "A case of granulomatous rosacea successfully treated with pimecrolimus cream", Journal of Dermatological Treatment, vol. 19, pp. 313-315 (2008).
Wester, et al., "Controlled release of benzoyl peroxide from a porous microsphere polymeric system can reduce topical irritancy", Journal of the American Academy of Dermatology, vol. 24, pp. 720-726 (1991).
Sawleshwarkar, et al., "Multicenter study to evaluate efficacy and irritation potential of benzoyl peroxide 4% cream in hydrophase base (Brevoxyl) in acne vulgaris," Indian Journal of Dermatology, Venereology and Leprology, vol. 69, pp. 19-22 (2003).
Breneman, et al., "Double -blind, randomized, vehicle-controlled clinical trial of once-daily benzoyl peroxide/clindamycin topical gel in the treatment of patients with moderate to severe rosacea," International Journal of Dermatology, vol. 43, pp. 381-387 (2004).
Gold, et al., P161 "Use of Benzoyl Peroxide/Clindamycin gel in the once daily treatment of moderate rosacea," Journal of the American Academy of Dermatology, vol. 52, suppl. p. 25 (2005).
Leyden, et al., P53 "Blinded photographic review for a double blind, multicenter, placebo-controlled study comparing Benzoyl Peroxide/Clindamycin and placebo for the treatment of rosacea," Journal of the American Academy of Dermatology, vol. 52, suppl. p. 14 (2004).
Goldgar, et al., "Treatment Options for Acne Rosacea," American Family Physician, vol. 80, pp. 461-468 (2009).
Crawford, et al., "Rosacea: 1. Etiology, pathogenesis, and subtype classification," Journal of the American Academy of Dermatology, vol. 51, pp. 327-341 (2004).
McGregor, et al., "A Review of the Current Modalities of the Treatment of Papulopustular Rosacea," Dermatologic Clinics, vol. 36, 16 pages (2018).
Feaster, et al., "Clinical effectiveness of novel rosacea therapies," Current Opinion in Pharmacology, vol. 46, pp. 14-18 (2019).
Del Rosso, et al., "Update on the Management of Rosacea from the American Acne & Rosacea Society (AARS)", The Journal of Clinical & Aesthetic Dermatology, vol. 12, pp. 17-24 (2019).
James, et al., "Rosacea", Andrews' Diseases of the Skin: Clinical Dermatology, 10th ed., Saunders Elsevier, pp. 239-248 (2005).
International Search Report and Written Opinion dated Aug. 28, 2020 in International Patent Application No. PCT/IB2020/00120, 15 pages.
International Search Report and Written Opinion dated Oct. 5, 2020 in International Patent Application No. PCT/IB2020/00119, 25 pages.

* cited by examiner

METHOD FOR PROVIDING EARLY ONSET OF ACTION IN THE TREATMENT OF ROSACEA

CROSS-REFERENCE TO RELATED APPLICATIONS

This application claims priority under 35 U.S.C. § 119(e) from U.S. Provisional Application No. 62/977,974, filed Feb. 18, 2020, U.S. Provisional Application No. 62/977,952, filed Feb. 18, 2020, U.S. Provisional Application No. 62/972,896, filed Feb. 11, 2020, U.S. Provisional Application No. 62/972,310, filed Feb. 10, 2020, U.S. Provisional Application No. 62/960,384, filed Jan. 13, 2020, U.S. Provisional Application No. 62/925,258, filed Oct. 24, 2019, U.S. Provisional 62/871,286, filed Jul. 8, 2019, U.S. Provisional 62/871,283, filed Jul. 8, 2019, U.S. Provisional 62/807,356, filed Feb. 19, 2019, and U.S. Provisional 62/807,368, filed Feb. 19, 2019, the contents of which are incorporated in their entirety as if fully set forth herein.

TECHNICAL FIELD

This application relates to methods for providing early onset of action in the therapeutic treatment of skin conditions and afflictions, such as rosacea and symptoms and considerations associated therewith, including topically applying to the skin of a subject in need of said treatment a pharmaceutical composition comprising benzoyl peroxide.

BACKGROUND

Rosacea is a chronic disease of inflammatory dermatitis that mainly affects the median part of the face and the eyelids of certain adults. It is characterized by telangiectatic erythema, dryness of the skin. papules and pustules. Conventionally, rosacea develops in adults from the ages of 30 to 50, and more frequently affects women, although the condition is generally more severe in men. Rosacea is a primitively vascular condition whose inflammatory stage lacks the cysts and comedones characteristic of common acne.

Factors that have been described as possibly contributing towards the development of rosacea include for example: the presence of parasites such as the *Demodex folliculorum*, the presence of bacteria such as *Helicobacter pylori* (a bacterium associated with gastrointestinal disorders), hormonal factors (such as endocrine factors), climatic and immunological factors, and so forth.

Rosacea develops in four stages over several years, in spasms aggravated by variations in temperature, alcohol, spices, exposure to sunlight and stress. The various stages of the disease are:

Stage 1 (stage of erythema episodes): the patients have erythrosis spasms due to the sudden dilation of the arterioles of the face, which then take on a congestive, red appearance. These spasms are caused by emotions, meals and temperature changes.

Stage 2 (stage of couperosis, i.e., of permanent erythema with telangiectasia): certain patients also have oedema on the cheeks and the forehead.

Stage 3 (inflammatory stage, papulopustular rosacea): patients exhibit appearance of inflammatory papules and pustules, but without affecting the sebaceous follicles, and thus, with absence of cysts and comedones.

Stage 4 (rhinophyma stage): this late phase essentially affects men. The patients have a bumpy, voluminous red nose with sebaceous hyperplasia and fibrous reordering of the connective tissue.

Typical treatment of rosacea includes oral or topical administration of antibiotics such as tetracyclines, salicylic acid, anti-fungal agents, steroids, metronidazole (an antibacterial agent) and isotretinoin, or even with anti-infectious agents such as azelaic acid.

SUMMARY

An exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising from about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 9% after about 2 weeks, and wherein the primary measure of success is defined as a 2-grade improvement in Investigator Global Assessment (IGA) of clear or almost clear.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 25% after about 4 weeks, and wherein the primary measure of success is defined as a 2-grade improvement in Investigator Global Assessment (IGA) of clear or almost clear.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4 or 8 weeks, wherein a primary measure of success in a group of subject is at least about 40% after about 8 weeks, and wherein the primary measure of success is defined as a 2-grade improvement in Investigator Global Assessment (IGA) of clear or almost clear.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a secondary measure of success in a group of such subjects is at least about 40% after at least about 2 weeks, and wherein the second measure of success is defined as mean inflammatory lesion count percent reduction from baseline.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a secondary measure of success in a group of such subjects is at least about 55% after at least about 4 weeks, and wherein the second measure of success is defined as mean inflammatory lesion count percent reduction from baseline.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a secondary measure of success in a group of such subjects is at least about 65% after at least about 8 weeks, and wherein the second measure of success is defined as mean inflammatory lesion count percent reduction from baseline.

Another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, and wherein the absolute reduction in lesion count after about 2 weeks is at least twice the absolute reduction in lesion count after about 4 weeks of treatment.

Another exemplary embodiment of this application is a pharmaceutical composition for use as a medicament for providing early onset of action in the therapeutic treatment rosacea, the pharmaceutical composition comprising from about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 9% after about 2 weeks, and wherein the primary measure of success is defined as a 2-grade improvement in Investigator Global Assessment (IGA) of clear or almost clear.

Another exemplary embodiment of this application is the use of a pharmaceutical composition for providing early onset of action in the treatment of rosacea, the pharmaceutical composition comprising from about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 9% after about 2 weeks, and wherein the primary measure of success is defined as a 2-grade improvement in Investigator Global Assessment (IGA) of clear or almost clear.

In other exemplary embodiments, the benzoyl peroxide is the sole active ingredient administered to the subject in need of said treatment during the duration of the regimen; the pharmaceutical composition comprises about 2.5% w/w to about 10% w/w of benzoyl peroxide, preferably about 5% w/w of benzoyl peroxide; the benzoyl peroxide is in a form selected from solid, solution or suspension; the regimen is a first-line therapy for the treatment of rosacea; the rosacea is any of erythematotelengietatic, papulopustular, phymatous or ocular rosacea; the pharmaceutical composition is a cream or an emulsion; the pharmaceutical composition is an extended release formulation; the extended-release effect is obtained by encapsulation, microencapsulation, microspheres or coating, preferably the benzoyl peroxide is encapsulated and/or microencapsulated and/or the benzoyl peroxide is included in a microsphere and/or a coating; and/or the regimen has an adverse events values similar to or lower than the adverse events values of a vehicle control.

In other exemplary embodiments, the reduction in total number of inflammatory lesion counts in a group of such subjects is a reduction of at least about 14 lesions after at least about 4 weeks of treatment; and/or the reduction in total number of inflammatory lesion counts in a group of such subjects is a reduction of at least about 17 lesions after at least about 8 weeks of treatment.

In other exemplary embodiments, the pharmaceutical composition can be used as a medicament in the first-line treatment of rosacea.

Details of other exemplary embodiments of the present disclosure will be included in the following detailed description and the accompanying drawings. It is appreciated that certain features of the exemplary embodiments described in this application, which are, for clarity, described in the context of separate embodiments, can also be provided in combination in a single embodiment.

BRIEF DESCRIPTION OF THE DRAWINGS

In order to understand the disclosure and to see how it can be carried out in practice, embodiments will now be described, by way of non-limiting examples only, with reference to the accompanying drawings, in which.

DETAILED DESCRIPTION

Figure 1:
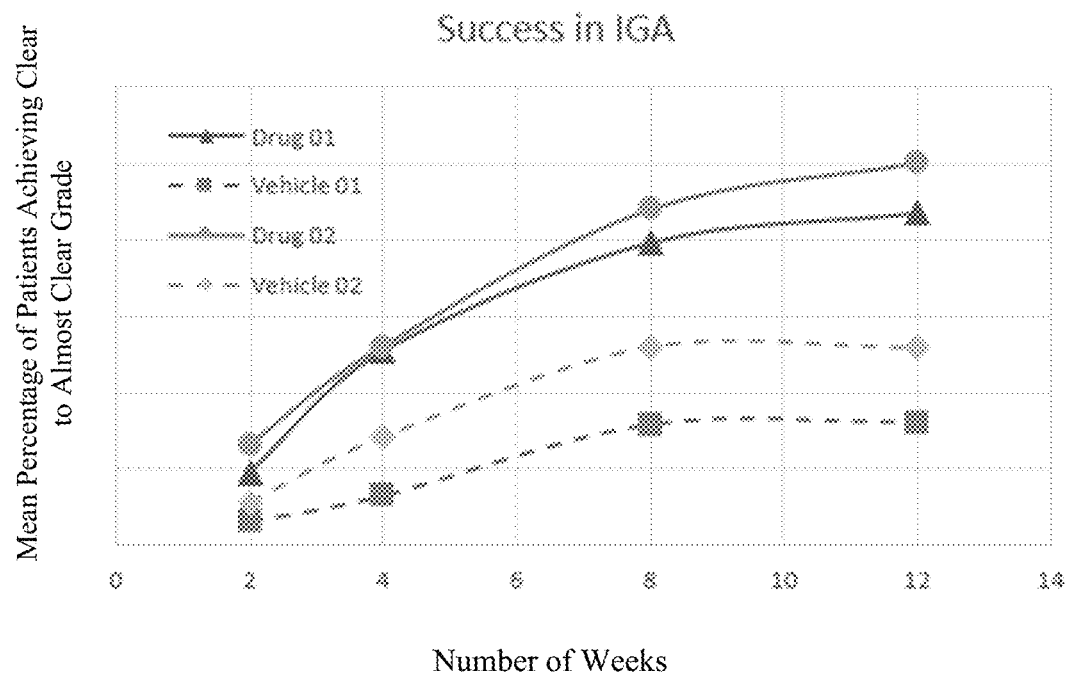
FIG. 1 is a graph presenting the IGA per time of administering BPO composition as compared with vehicle alone over a period of time of 12 weeks.

Multiple studies have been directed to the treatment of rosacea using a pharmaceutical or dermatological active agent such as metronidazole, azelaic acid, sulfacetamide, brimonidine, ivermectin, permethrin and clindamycin, and with doxycycline, which is identified as the only FDA-approved treatment for rosacea (Oge et al., "Rosacea: Diagnosis and Treatment," *American Family Physician*, v. 92(3), pp. 187-198 (2015); Gul et al., "A case of granulomatous rosacea successfully treated with pimecrolimus cream," *J. Derm. Treatment*, 19, 313-315 (2008)).

Benzoyl peroxide (BPO) is generally identified as an anti-acne agent, used alone (U.S. Pat. No. 9,439,857; Wester et al., "Controlled release of benzoyl peroxide from a porous microsphere polymeric system can reduce topical irritancy," *J. Am. Acad. Derma.* 24, 720-726 (1991); Sawleshwarkar, "Multicenter study to evaluate efficacy and irritation potential of benzoyl peroxide 4% cream in hydrophase base (Brevoxyl) in acne vulgaris," *Ind. J. Derm. Vener. Lepro.*, 69(1), 19-22 (2003)) or in combination with a primary active such as avermectin (U.S. 2011/0052515).

One such study includes a therapeutic regimen involving treatment of acne rosacea in a group of patients in need of such treatment with 5% BPO-acetone gel for four weeks, followed by treatment of the same group of patients with 10% BPO-acetone gel for an additional four weeks. (Montes et al., "Topical Treatment of Acne Rosacea with Benzoyl Peroxide Acetone Gel," *Therapeutics for the Clinician: New Reports on Treatment Modalities of Possible Interest to Patient-Caring Physicians*, 32, 185-190 (1983)). The Montes study showed a significantly better response during the five to eight weeks of treatment with 10% BPO-acetone gel compared to the first four weeks of treatment with 5% BPO-acetone gel. Moreover, although Montes 1983 claims success in the treatment of rosacea using a BPO-acetone gel, 25% of the patients in the study showed no improvement and 40% of the patients developed an irritation. Additionally, this study required increasing the amount of BPO administered to the patients from 5% to 10% after week four. The results of the Montes 1983 study make it clear that BPO would not be suitable for regular use in the treatment of rosacea, especially as a first line treatment of rosacea.

Other studies show that, when used in the treatment of rosacea, BPO is generally combined with a primary active agent such as clindamycin (Breneman et al., "Double-blind, randomized, vehicle-controlled clinical trial of once-daily benzoyl peroxide/clindamycin topical gel in the treatment of patients with moderate to severe rosacea," *Int. J. Derm.*, 43, 381-387 (2004); Gold et al., "Use of Benzoyl Peroxide/Clindamycin gel in the once daily treatment of moderate rosacea," *J. Amer. Acad. Dermat.*, 52(3), sup., P25 (2004); Leyden et al., "Blind photographic review for a double blind, multicenter, placebo-controlled study comparing Benzoyl Peroxide/Clindamycin and placebo for the treatment of rosacea," *J. Amer. Acari Dermat.*, 52(3), sup., P14 (2004); Goldgar et al., "Treatment Options for Acne Rosacea," *J Amer. Fam. Physician*, 80(5), 461-468 (2009)).

BPO is generally identified as only a possible second-line treatment of rosacea following the use of another, different active. (Oge 2015, Table 5; Goldgar 2009, "Key Recommendations for Practice"). Goldgar 2009, in particular, recommends the use of BPO only as a tertiary therapy for the treatment of rosacea.

When BPO was used as the sole active agent for the treatment of rosacea, lesions were found to be unresponsive. (Gul 2008).

These previous rosacea treatments with BPO alone or in combination with other agents, have been shown to have severe drawbacks such as irritation and intolerance phenomena, especially when they are administered for a prolonged period. (Crawford et al., "Rosacea: I. Etiology, pathogenesis, and subtype classification," *J. Am. Acad. Dermatol.*, 51, 327-341 (2004)). These treatments are only suppressive and not curative, acting especially on the pustulous spasms occurring during the inflammatory stage.

Such drawbacks associated with the treatment of rosacea involving the use of BPO result in exclusion of BPO from standard rosacea treatment methods. For example, "A Review of the Current Modalities for the Treatment of Papulopustular Rosacea" identifies metronidazole, ivermectin and azelaic acid as topical therapies that were proven effective for the treatment of rosacea. (McGregor et al., "A Review of the Current Modalities of the Treatment of Papulopustular Rosacea," *Dermatol. Clin.* (2017)). While McGregor 2017 mentions alternate therapies, such as sodium sulfacetanide/sulfur cream, clindamycin, tretinoin, calcineurin inhibitors and oral tretinoin, that may have some effectiveness in the treatment of rosacea, notably, McGregor 2017 does not include, or even mention, BPO in the long list of possible treatment therapies described therein. The absence of BPO as a known treatment for rosacea is also evident in other studies. (Feaster et al., "Clinical effectiveness of novel rosacea therapies," *Current Op. Pharmacol.*, 46, 14-18 (2019); Del Rosso et al., "Update on the Management of Rosacea from the American Acne & Rosacea Society (AARS); *J. Clinical & Aesthetic Derma*, 12 (6), 17-24 (2019)). The absence of BPO as a recognized first-line treatment for rosacea is especially evident in Del Rosso, which is a well-known and respected authority on the treatment of rosacea. The AARS review lists the Society's recommendation for rosacea treatment, including topical metronidazole, topical azelaic acid, oral tetracyclines, ivermectin, topical alpha agonists, and oral isotretinoin, as well as "alternative therapies," such as sulfacetamide/sulfur, calcineurin inhibitors, retinoids, and permethrin. (See e.g., Table 1 of the AARS review.) BPO is not mentioned in the AARS review either as a leading, or even an alternative, therapeutic agent for the treatment of rosacea.

Considering the chronic nature of rosacea, there is a need for early onset of action, and a prolonged use treatment of the disease, its symptoms and associated conditions, in a safe and effective manner. Thus, there exists a need for compositions that show early onset of action, and improved efficacy in the treatment of rosacea, that impart greater tolerance to the active principles and that reduce, substantially minimize or do not have the side effects described in the prior art.

Advantages and features of the present disclosure, and methods for accomplishing the same will be more clearly understood from exemplary embodiments described below with reference to any accompanying drawings. However, the present disclosure is not limited to the following exemplary embodiments and can be implemented in various different forms. The exemplary embodiments are provided only to provide sufficient disclosure of the present discoveries and to fully provide a person having ordinary skill in the art to which the present disclosure pertains within the technical field, and the present disclosure will be defined by any appended claims and combinations thereof.

As used herein, like reference numerals generally denote like elements throughout the present specification. Further, in the following description, a detailed explanation of well-known related technologies can be omitted to avoid unnecessarily obscuring the subject matter of the present disclosure.

As used herein, terms such as "including" and "having" are generally intended to allow other components to be included unless the terms are used in conjunction with the term "only."

As used herein, the term "topical use" is meant to encompass the topical administration of an exemplary composition by formulating said composition in any way known in the art, or in formulations disclosed herein, which are compatible with the skin, mucous membranes and/or the integuments.

As used herein, the term "treating" or "treatment" includes curing a condition, treating a condition, preventing or substantially preventing a condition, treating symptoms of a condition, curing symptoms of a condition, ameliorating, reducing and/or minimizing symptoms of a condition, treating effects of a condition, ameliorating, reducing and/or minimizing effects of a condition, and preventing and/or substantially preventing results of a condition, As used herein, the term "first-line therapy" or "first-line treatment" means a therapy or treatment for which its label does not include a requirement or recommendation that said therapy or treatment should be used only after other therapies or treatments were shown to be unsatisfactory or unsuccessful. It can also include a therapy and/or treatment wherein no other actives (beyond the main active) are administered to the individual subject in need.

As used herein, the term "early onset" or "early onset of action" means achieving a desired result and/or effect at a point in time that is earlier or even much early than achieved using a vehicle or other, conventional treatment approach. For example, it can mean achieving a desired result and/or effect no later than about 8 weeks from initial treatment, preferably no later than about 4 weeks from initial treatment, and more preferably no later than about 2 weeks from initial treatment.

As used herein, the term "pharmaceutical composition" refers to a composition comprising one or more active ingredients with other components such as, for example, pharmaceutically acceptable ingredients and/or excipients. The purpose of a pharmaceutical composition is to facilitate administration of an active ingredient to a subject.

As used herein, the terms "pharmaceutically active agent" or "active agent" or "active pharmaceutical ingredient" are interchangeable and mean the ingredient is a pharmaceutical drug, which is biologically- and/or chemically-active and is regulatory-approved or approvable as such.

As used herein, the term "ingredient" refers to a pharmaceutically acceptable ingredient, which is included or is amenable to be included in The FDA's Inactive Ingredient (IIG) database. Inactive ingredients can sometimes exhibit some therapeutic effects, although they are not drugs.

As used herein, the term "adverse events values" refers to an average percentage of subjects that experience any adverse events associated with the treatment of rosacea with a composition described and/or claimed herein (usually on a surface of the skin of a subject treated with a composition described and/or claimed herein). A non-limiting list of such adverse events includes: irritation, dryness, scaling, itching purities, burning, stinging, combinations thereof and the like.

Whenever a numerical range is indicated herewith, it is meant to include any cited numeral (fractional or integral) within the indicated range. The phrases "ranging/ranges between" a first indicated number and a second indicated number and "ranging/ranges from" a first indicated number "to" a second indicated number are used herein interchangeable and are meant to include the first and second indicated numbers and all fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 µm" is intended to mean "about 10 µm."

As used herein, numbers and/or numerical ranges preceded by the term "about" should not be considered to be limited to the recited range. Rather, numbers and/or numerical ranges preceded by the term "about" should be understood to include a range accepted by those skilled in the art for any given element in formations according to the subject invention.

As used herein, when a numerical value is preceded by the term "about," the term "about" is intended to indicate +/−10%.

As used herein, the singular form "a," "an" and "the" include plural references unless the context clearly dictates otherwise. For example, the term "a compound" or "at least one compound" can include a plurality of compounds, including combinations and/or mixtures thereof.

As used herein, the term "method" refers to manners, means, techniques and procedures for accomplishing a given task including, but not limited to, those manners, means, technical and procedures either known to, or readily developed from known manners, means, techniques and procedures by practitioners of the chemical, pharmacological, biological, biochemical and medical arts.

It is appreciated that certain features of the exemplary embodiments described herein, which are, for clarity, described in the context of separate embodiments, can also be provided in combination in a single embodiment. Conversely, various features of the exemplary embodiments, which are, for brevity, described in the context of a single embodiment, can also be provided separately or in any suitable sub-combination or as suitable in any other described embodiment. Certain features described in the context of various embodiments are not to be considered essential features of those embodiments, unless the embodiment is inoperative without those elements.

An exemplary embodiment of this application is regimen for the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, to achieve, in a group of such subjects, a primary measure of success of at least about 9%, wherein said pharmaceutical composition is applied once daily for a period of at least about 2 weeks, and wherein the primary measure of success is defined as a 2-grade improvement in Investigator Global Assessment (IGA) of clear or almost clear.

The success in IGA, a primary measure of success, after topical application of BPO as a first-line of treatment for at least about 2 weeks can be at least about 8%, preferably from about 9% to about 15%, and more preferably from about 9% to about 13%.

The success in IGA, a primary measure of success, after topical application of a pharmaceutical composition including BPO as a first-line of treatment for at least about 4 weeks can be at least 20%, preferably from about 20% to about 40%, preferably from about 25% to 35%, preferably from about 25% to about 32%, and more preferably about 25%.

The success in IGA, a primary measure of success, after topical application of a pharmaceutical composition including BPO as a first-line of treatment for at least about 8 weeks can be at least about 30%, preferably from about 30% to about 50%, from about 35% to about 45%, more preferably about 40%.

The success in IGA, a primary measure of success, after topical application of a pharmaceutical composition including BPO as a first-line of treatment for at least about 12 weeks can be at least about 30%, preferably from about 30% to about 50%, from about 35% to about 50%, more preferably about 47%.

In another exemplary embodiment, the benzoyl peroxide is the only active ingredient in said pharmaceutical composition and/or in the regimen and/or in the method of treatment. In another exemplary embodiment, the benzoyl peroxide is the sole active ingredient administered to the subject during the duration of the regimen.

In another exemplary embodiment, the pharmaceutical composition comprises about 2.5% w/w to about 10% w/w of benzoyl peroxide, preferably about 3.0% to about 10% of benzoyl peroxide, more preferably about 3% to about 5% of benzoyl peroxide, and more preferably about 5% w/w of benzoyl peroxide.

In another exemplary embodiment, the benzoyl peroxide is in a form selected from solid, solution, and suspension.

In another exemplary embodiment, the regimen is a first-line therapy for the treatment of rosacea.

In another exemplary embodiment, the rosacea is any of erythematotelengietatic, papulopustular, phymatous or ocular rosacea.

In another exemplary embodiment, the pharmaceutical composition is a cream, cream gel, an emulsion, a gel or a foam; preferably a cream or an emulsion.

In another exemplary embodiment, the pharmaceutical composition can be an extended—and/or controlled-release formulation, and the extended-release and/or controlled-release effect is obtained by any one of encapsulation, microencapsulation, microspheres and/or coating, or can be encapsulated and/or microencapsulated or included in a microsphere and/or a coating.

In another exemplary embodiment, the regimen surprisingly exhibits adverse events values similar to, or even less than, the adverse events values of a vehicle control.

Yet another exemplary embodiment of this application is a regimen for the therapeutic treatment of rosacea, which includes topically applying to the skin of a subject in need of said treatment a pharmaceutical composition including about 1% to about 10% benzoyl peroxide as an active ingredient, and a pharmaceutically acceptable carrier or excipient, to achieve, in a group of such subjects, wherein the benzoyl peroxide is the only active ingredient in said pharmaceutical composition and/or in said regimen.

Yet another exemplary embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% to about 10% benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a secondary measure of success in a group of such subjects is at least about 40% at one of the corresponding time points, and wherein the second measure of success is defined as mean inflammatory lesion count percent reduction from previous measurement.

Yet another embodiment of this application is a regimen for providing early onset of action in the therapeutic treatment of rosacea, the regimen comprising topically applying to the skin of a subject in need of the treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in the pharmaceutical composition, wherein the pharmaceutical composition is applied once daily for a period of at least about 2, 4, 8 or 12 weeks, wherein a secondary measure of success in a group of such subjects is at least about 55% after at least about 4 weeks, and wherein the second measure of success is defined as mean inflammatory lesion count percent reduction from baseline.

Yet another embodiment of this application is a regimen for providing early onset of action in the therapeutic treatment of rosacea, the regimen comprising topically applying to the skin of a subject in need of the treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in the pharmaceutical composition, wherein the pharmaceutical composition is applied once daily for a period of at least about 2, 4, 8 or 12 weeks, wherein a secondary measure of success in a group of such subjects is at least about 65% after at least 8 weeks, and wherein the second measure of success is defined as mean inflammatory lesion count percent reduction from baseline. In some embodiments, the benzoyl peroxide is the sole active ingredient administered to the subject in need of the treatment during the duration of the regimen. In some embodiments, the reduction in total number of inflammatory lesion counts in a group of such subjects is at least about 14 lesion reduction after at least about 4 weeks of treatment. In some other embodiments, the reduction in total number of inflammatory lesion counts in a group of such subjects is at least about 17 lesion reduction after at least 8 weeks of treatment.

Yet another embodiment of this application is a regimen for providing early onset of action in the therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein the pharmaceutical composition is applied once daily for a period of at least about 2, 4, 8 or 12 weeks, and wherein the absolute reduction in lesion count after 2 weeks is at least twice the absolute reduction in lesion count after about 4 weeks of treatment.

Yet another embodiment of this application is a first-line treatment regimen for the therapeutic treatment of rosacea, including topically applying to the skin of a subject in need of said treatment a pharmaceutical composition, the pharmaceutical composition comprising about 1% to about 10% benzoyl peroxide as an active ingredient, and a pharmaceutically acceptable carrier or excipient, to achieve, in a group of such subjects, a primary measure of success of at least about 9%, wherein the benzoyl peroxide is the only active ingredient in said pharmaceutical composition and/or in said regimen, wherein said pharmaceutical composition is applied once daily for a period of at least about 2 weeks and wherein the primary measure of success is defined as a 2-grade improvement in Investigator Global Assessment (IGA) of clear or almost clear.

Yet another exemplary embodiment of this application is a first-line treatment regimen for the therapeutic treatment of rosacea, the regimen comprising topically applying to the skin of a subject in need of said treatment a pharmaceutical composition, the pharmaceutical composition comprising about 1% to about 10% benzoyl peroxide as an active ingredient, and a pharmaceutically acceptable carrier or excipient, to achieve, in a group of such subjects, a secondary measure of success of at least about 40%, wherein the benzoyl peroxide is the only active ingredient in said pharmaceutical composition and/or in said regimen, wherein said pharmaceutical composition is applied once daily for a period of at least about 2 weeks and wherein the secondary measure of success is defined as a percentage decrease the in the number of inflammatory lesions.

Yet another exemplary embodiment of this application is a treatment regimen for the therapeutic treatment of rosacea, the regimen comprising topically applying to the skin of a subject in need of said treatment a pharmaceutical composition, the pharmaceutical composition comprising about 1% to about 10% benzoyl peroxide as an active ingredient, and a pharmaceutically acceptable carrier or excipient, to achieve, in a group of such subjects, wherein the pharmaceutical composition is physically and/or chemically stable for a period of at least about 12 weeks.

In some embodiments, said rosacea is papulopustular rosacea (i.e., inflammatory rosacea; Rapini et al. (2007). *Dermatology: 2-Volume Set*. St. Louis: Mosby and James, William et al. (2005). *Andrews' Diseases of the Skin: Clinical Dermatology*. (10th ed.). Saunders p. 245).

Yet another embodiment of this application is a pharmaceutical composition for use as a medicament for the treatment rosacea, the pharmaceutical composition comprising from about 1% to about 10% benzoyl peroxide as an active ingredient, preferably about 2.5% w/w to about 10% w/w, preferably about 3% w/w to about 5% w/w of benzoyl peroxide, more preferably about 5% benzoyl peroxide, and a pharmaceutically acceptable carrier or excipient, wherein said pharmaceutical composition is applied once daily for a period of at least about 2 weeks, at least about 4 weeks, at least about 8 weeks or at least about 12 weeks. The pharmaceutical composition can include benzoyl peroxide as the only active ingredient, and the benzoyl peroxide can be the sole active ingredient administered to the subject in need of said treatment during the duration of the regimen. The pharmaceutical composition can be used as a medicament in the first-line treatment of rosacea.

Yet another embodiment of this application is use of a pharmaceutical composition for the treatment of rosacea, the pharmaceutical composition comprising from about 1% to about 10% benzoyl peroxide as an active ingredient, preferably about 2.5% w/w to about 10% w/w, preferably about 3% w/w to about 5% w/w of benzoyl peroxide, more preferably about 5% benzoyl peroxide, and a pharmaceutically acceptable carrier or excipient, wherein said pharmaceutical composition is applied once daily for a period of at least about 2 weeks, at least about 4 weeks, at least about 8 weeks or at least about 12 weeks. The pharmaceutical composition can include benzoyl peroxide as the only active ingredient, and the benzoyl peroxide can be the sole active ingredient administered to the subject in need of said treatment during the duration of the regimen. The pharmaceutical composition can be used in the first-line treatment of rosacea.

Yet another embodiment of this application is a pharmaceutical composition for use as a medicament for providing early onset of action in the therapeutic treatment rosacea, the pharmaceutical composition comprising from about 1% w/w to about 10% w/w benzoyl peroxide, preferably about 2.5% w/w to about 10% w/w, preferably about 3% w/w to about 5% w/w benzoyl peroxide, more preferably about 5% w/w benzoyl peroxide, as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 9% after about 2 weeks or a secondary measure of success in a group of such subjects is at least about 40% after at least about 2 weeks, wherein the primary measure of success is defined as a 2-grade improvement in Investigator Global Assessment (IGA) of clear or almost clear wherein the second measure of success is defined as mean inflammatory lesion count percent reduction from baseline. The benzoyl peroxide can be the sole active ingredient administered to the subject in need of said treatment during the duration of the regimen. The pharmaceutical composition can be used in the first-line treatment of rosacea.

Yet another embodiment of this application is use of a pharmaceutical composition for providing early onset of action in the treatment of rosacea, the pharmaceutical composition comprising from about 1% w/w to about 10% w/w benzoyl peroxide as an active ingredient, preferably from about 2.5% w/w to about 10% w/w benzoyl peroxide, preferably 3% w/w to about 5% w/w benzoyl peroxide, more preferably 5% w/w benzoyl peroxide, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein a primary measure of success in a group of subject is at least about 9% after about 2 weeks or a secondary measure of success in a group of such subjects is at least about 40% after at least about 2 weeks, wherein the primary measure of success is defined as a 2-grade improvement in Investigator Global Assessment (IGA) of clear or almost clear wherein the second measure of success is defined as mean inflammatory lesion count percent reduction from baseline. The benzoyl peroxide can be the sole active ingredient administered to the subject in need of said treatment during the duration of the regimen. The pharmaceutical composition can be used in the first-line treatment of rosacea.

In some embodiments, the adverse effects after topical administration of BPO are comparable to the adverse effects after topical administration of a vehicle, and in some embodiments, the adverse effects after topical administration of BPO are less than the adverse effects after topical administration of a vehicle. In other embodiments, the number of rosacea patients demonstrating no or almost no subcutaneous reactions after treatment with BPO increases weekly despite prolonged, weekly use of BPO in the treatment of rosacea.

In some further embodiments, the composition further comprises at least one non pharmaceutical active additive selected from the group consisting of chelating agents, antioxidants, sunscreens, preservatives, fillers, electrolytes, humectants, dyes, mineral or organic acids or bases, fragrances, essential oils, moisturizers, vitamins, essential fatty acids, sphingolipids, self-tanning compounds, calmatives and skin-protecting agents, pro-penetrating agents and gelling agents, or a mixture and/or combination thereof.

In other embodiments, the composition is formulated into a topically applicable, physiologically acceptable medium comprising of: (a) at least one member selected from the group consisting of water, alcohols, oils, fatty substances and waxes; and (b) at least one additive selected from the group consisting of chelating agents, antioxidants, sunscreens, preservatives, fillers, electrolytes, humectants, dyes, mineral acids, mineral bases, organic acids, organic bases, fragrances, essential oils, moisturizers, vitamins, essential fatty acids, sphingolipids, self-tanning compounds, calmatives, skin-protecting agents, pro-penetrating agents, gelling agents, emulsifiers, co-emulsifiers, and mixtures and/or combinations thereof.

In some embodiments the composition is formulated as an emulsion (including an oil-in-water emulsion, a water-in-oil emulsion, multiple emulsions and microemulsions). In other embodiments, the composition is formulated as a cream.

The compositions described in exemplary embodiments herein are pharmaceutical compositions, and especially dermatological compositions, which can be in any galenical form conventionally used for topical application. By addition of a fatty or oily phase, they can also be in the form of dispersions of the lotion or serum type, emulsions of liquid or semi-liquid consistency of the milk type obtained by dispersing a fatty phase in an aqueous phase (O/W) or conversely (W/O), or suspensions or emulsions of soft, semiliquid or solid consistency of the cream, gel or ointment type, or alternatively multiple emulsions (W/O/W or O/W/O), microemulsions, microcapsules, microparticles and/or vesicular dispersions of ionic and/or nonionic type, and/or wax/aqueous phase dispersions. These compositions are formulated according to the usual methods.

In further embodiments, the composition comprises, as a single pharmaceutical active agent, benzoyl peroxide in a solid form, for topical use in the treatment of rosacea, is an oil in water emulsion comprising a polyoxylstearate and a glycerylstearate. Various methods for the preparation of the BPO-containing compositions are described in U.S. Application Publication Nos. 2010/0016443, 2017/0281571 and 2018/0147165 and U.S. Pat. No. 9,687,465.

In some embodiments, the ratio of said polyoxylstearate to said glycerylstearate is in the range of about 0.1:10 to about 10:0.1.

In yet further embodiments, said polyoxylstearate is selected from the group consisting of Polyoxyl-8 stearate, Polyoxyl-20 stearate, Polyoxyl-40 stearate, Polyoxyl-100 stearate and combinations and/or mixtures thereof.

In further embodiments, said glycerylstearate is selected from the group consisting of glyceryl mono-stearate, glyceryl di-stearate and combinations and/or mixtures thereof.

In other embodiments, said polyoxylstearate in said composition is in the range of from about 0.1% w/w to about 30% w/w.

In further embodiments, the amount of said glycerylstearate in said composition is in the range of from about 0.1% w/w to about 30% w/w.

In other embodiments, said composition further comprises at least one fatty alcohol.

In other embodiments, said at least one fatty alcohol is selected from the group consisting of octyl alcohol, 2-ethyl hexanol. nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol. behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and combinations and/or mixtures thereof.

In further embodiments, the amount of said at least one fatty alcohol in said composition is in the range of from about 0.2% w/w to about 50% w/w.

In yet other embodiments, said composition further comprises a polyacrylic acid homopolymer or copolymer.

In other embodiments, said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and combinations and/or mixtures thereof.

In further embodiments, said oil in present in the composition in an amount in the range of from about 0.05% w/w to about 50% w/w.

In some embodiments, said water in said oil in water emulsion further comprises at least one water soluble humectant.

In other embodiments, said at least one water soluble humectant is selected from the group consisting of propylene glycol, glycerin, polyethylene glycol-X and combinations and/or mixtures thereof, where X is in the range of from about 200 to about 10,000.

In some embodiments, the composition comprises said solid BPO in a controlled and/or slowed release drug delivery system. In further embodiments, said controlled and/or slowed release drug delivery system is an encapsulation in a microcapsule, wherein said solid BPO is embedded in said microcapsule. When referring to a "controlled and/or slowed release drug delivery system" it should be understood to relate to a delivery system (which in the present application is a topical delivery system) that enables the release of the pharmaceutical active agent in predetermined amounts over a specified period. In some embodiments, said system is a core-shell system of a microcapsule and/or a porous matrix structure, such as, for example, a microsponge. The term "embedded" should be understood to encompass an inert system that provides a barrier between the pharmaceutical active agent, i.e. BPO, and its surrounding environment in the composition. In some embodiments, said agent is entrapped and/or encapsulated in said controlled release system.

In some embodiments, said core of said microcapsule comprises or consists of said solid BPO.

In some further embodiments, said microcapsules are a core shell microcapsule. The shell comprises at least one inorganic polymer. In some other embodiments, said inorganic polymer of said shell is a metal oxide or semi-metal oxide shell (layer).

In some embodiments, said microcapsule comprises a metal oxide or semi-metal oxide coating or layer (shell) and a core comprising or consisting of solid BPO.

In some embodiments, said microcapsule comprises a metal oxide or semi-metal oxide coating or layer (shell) and a core comprising solid BPO is prepared by a process comprising the steps of:

(a) contacting a solid BPO particulate matter with an ionic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide layer thereon thereby to obtain particulate matter coated by a metal oxide coating layer;

(c) repeating step (b) at least 4 more times: and (d) aging said coating layer.

As used herein, the term "solid BPO particulate matter" refers to a solid BPO having solubility in water of less than about 1% w/w, typically less than about 0.5% and at times less than about 0.1% w/w at room temperature (about 20° C.). The "solid BPO particulate matter" constitutes the "core" of the particles obtained by the process. The solid BPO particulate matter, is, in some embodiments, in such a state of subdivision that it can be suspended in water, e.g., in the form of a finely-divided powder having a $D_{90}$ (see definition below), in some embodiments in the range of from about 0.3 to about 50 microns. Such a particulate matter can be readily suspended in an aqueous systems by stirring, with or without the aid of a surfactant.

The terms "solid BPO particulate matter" and "particulate matter" will be used interchangeably.

In the present application, the terms "layer", "coating" or "shell" and similar terms, refer to a layer of metal oxide or semi-metal oxide formed around a particle or particulate matter. The layer or coating need not always be complete or uniform and need not necessarily lead to complete coverage of the particulate matter or particle surface. It is appreciated that upon repetition of the coating steps as the coating process proceeds a more uniform coating and more complete coverage of the particulate matter is obtained.

The term "dispersion," as used herein, in step (a) of the process refers to a solid dispersion of the particulate matter in the aqueous medium. Step (a) of the process can further comprise reducing the particle size of the particulate matter to the desired particle size, for example, by milling or homogenization.

The core (i.e., solid, BPO particulate matter) can be of any shape, for example, rod-like, plate-like, ellipsoidal, cubic, spherical shape, combinations thereof and the like.

Reference to the size of particles will be made through their $D_{90}$, which means that about 90% of the particles have the stated dimension or less (measured by volume). Thus, for example, for spherical particles stated to have a diameter of about 10 micrometer ("microns"), this means that the particles have a $D_{90}$ of about 10 microns. The $D_{90}$ can be measured by laser diffraction. For particles having a shape other than spheres, the $D_{90}$ refers to the mean average of the diameter of a plurality of particles.

In the case of cores having a spherical shape, the $D_{90}$ can be in the range of from about 0.3 to 90 microns, in some embodiments from about 0.3 to about 50 microns, in some other embodiments from about 1 to about 50 microns, in some further embodiments from about 5 to about 30 microns. By the term "$D_{90}$ can be in the range of from about 0.3 microns to about 90 microns" is meant that about 90% by volume of the particles (in this case the particle's core) can be less than or equal to a value in the range of from about 0.3 microns to about 90 microns.

For generally cubic-shaped cores or cores having a shape resembling that of a cube, the mean size of a side can be in the range of from about 0.3 to about 80 microns, in some embodiments from about 0.3 to about 40 microns, in some further embodiments from about 0.8 to about 40 microns, in some further embodiments from about 4 to about 15 microns.

For rod-like shaped, ellipsoidal-shaped and plate-like shaped cores, the largest dimension (that of the longest axis) is typically in the range of from about 10 to about 100 microns, in some embodiments from about 15 to about 50 microns; and the smallest dimension is typically in the range of from about 0.5 to about 20 microns, in some further embodiments from about 2 to about 10 microns.

As used herein, unless otherwise indicated, the term "particle" refers to the metal oxide or semi-metal oxide coated particulate matter.

It is appreciated that some of the particles obtained by the process can at times be formed from two or more original particles of the solid BPO particulate and can accordingly include at times more than one core, such cores being separated from each other by a metal oxide region.

The weight of the solid BPO particulate (core material) based on the total weight of the particle can be in the range of from about 99% w/w to about 50% w/w, in some embodiments in the range of from about 97% w/w to about 50% w/w. The core material can be in a crystalline form, amorphous form, or combination thereof. The core material can be a cosmetic, pharmaceutical or an agrochemical active ingredient.

EXEMPLARY EMBODIMENTS

BPO-containing compositions were prepared following the various preparation methods described in U.S. Application Publication Nos. 2010/0016443, 2017/0281571 and 2018/0147165 and U.S. Pat. No. 9,687,465, the contents of which are incorporated herein, by reference, in their entirety.

Example 1: Efficacy Study of BPO as First-Line Treatment of Rosacea

Description: A multi-center, double-blind, randomized, vehicle-controlled, dose-range study of encapsulated 5% benzoyl peroxide (E-BPO) Cream and vehicle cream was performed to assess the efficacy and safety of E-BPO compared to vehicle. Study duration was 12 weeks and included approximately 350 male and female patients afflicted with papulopustular rosacea. Patients were at least 18 years of age, and met the inclusion/exclusion criteria described herein.

Dosing: Patients were randomized in a 2:1 ratio to the study product or vehicle treatment group, respectively. Patients applied the study product once daily for 12 weeks on the face (chin, left cheek, right cheek, nose, left forehead and right forehead) in a thin layer to provide even distribution, and avoid the eyes, lips, inside the nose, mouth and all mucous membranes.

Clinical and Safety Evaluations will be performed at:
1. Visit 1/Screening
2. Visit 2/Baseline, Day 1
3. Visit 3/Week 2, Day 15 (±3 Days)
4. Visit 4/Week 4, Day 29 (+3 Days)
5. Visit 5/Week 8, Day 57 (±3 Days)
6. Visit 6/Week 12, Day 85 (±4 Days)/End of Treatment/End of Study)

Patients were admitted into the study after meeting all inclusion/exclusion criteria, including a clinical diagnosis of rosacea and after written informed consent has been obtained. Subjects with severe rosacea who are appropriate for systemic treatment need to be counseled regarding their treatment options by the Principal Investigator. At each visit, a 5-point IGA scale of rosacea; rosacea erythema, and telangiectasia; and inflammatory (papules, pustules) lesion counts were performed and recorded.

Safety was assessed at all visits, and will include monitoring of local adverse experiences, Investigator Cutaneous Safety Assessment rating of dryness and scaling and Local Tolerability Assessment rating of itching and burning/stinging on a scale ranging from 0 (None) to 3 (Severe); patients complete a Patient Reported Outcomes (PRO) questionnaire at Visit 2, 3, 4, 5 and 6 and Rosacea Quality of Life Questionnaire (RosaQoL) at Baseline and Visit 6 or at early termination. Standardized photography of facial rosacea at Visit 2, 3, 4, 5 and 6 was performed at select site(s).

In addition to IGA, at each visit, the following safety measures were recorded: monitoring for any AE (adverse effects) including local and systemic; investigator Cutaneous Safety Assessment rating of erythema, dryness and scaling and Local Tolerability Assessments rating of itching and burning/stinging on a scale ranging from 0 (None) to 3 (Severe).

Urine pregnancy tests were performed on females of child-bearing potential at Screening, Baseline and every 4 weeks during study or at early termination. Regardless of the duration of the study, patients that exhibit serious adverse event (SAE) were followed up until the SAE resolved based on investigator's medical judgement.

Evaluation of efficacy: The first application of the test product was applied at the investigational site at the end of the Baseline visit (Day 0) under the supervision and instruction of the designated investigational site staff. The investigator performed the Investigator Global Assessment (IGA) and inflammatory lesion (papules and pustules) counts at Screening, Baseline, and Weeks 4, 8, and 12 (end of study) and erythema and telangiectasia assessments at Baseline, and Weeks 4, 8, and 12 (end of study). The evaluator also assessed local application site irritation (dryness, scaling, pruritus, stinging and burning) at Baseline and Weeks 2, 4, 8 and 12 (end of study). At selected investigational site(s), standardized photography of facial rosacea also was performed at Baseline and Week 8 and 12 (end of study).

The absolute change (primary measure of success) and percent change (secondary measure of success) from baseline of inflammatory lesions was derived for each patient at Weeks 2, 4, 8 and 12. The IGA was recorded for each patient at Baseline, Weeks 2, 4, 8 and 12. Weeks 2, 4, 8 and 12 with a patient were considered a success for those visits if the IGA was at least 2 grades less than baseline and are Clear or Almost Clear. Data from two sets of experiments—Drug 01+Vehicle 01 and Drug 02+Vehicle 02—are included herewith for each measurement Safety Assessments: Safety was evaluated by tabulations of adverse events (AEs), Cutaneous Safety Assessments for dryness and scaling, assessments for scores (erythema and telangiectasia) and Patient Global Impression of Treatment Side-Effects (PGI-SE) will be presented with descriptive statistics at Baseline and at the scheduled study visits. Frequencies and percentages for each outcome category will be included in these statistics.

Results:
Baseline Characteristics:
The Baseline characteristics were similar among the treatment groups. Patients selected for the treatment groups of this study suffered from moderate and severe rosacea, with a numerically higher percentage of subjects suffering from moderate rosacea. The baseline numerical percentage of treatment groups suffering from moderate and severe rosacea were similar for 5% E-BPO Cream and for Vehicle Cream.

Primary Efficacy Analyses:
The proportions of subjects with a primary measure of success (defined as a 2-grade improvement in the IGA relative to Baseline at Weeks 2, 4, 7 and 12, with an IGA of clear or almost clear) are shown in Tables 1A and 1B, and FIG. 1.

The mean percentage of patients (average value from two studies) achieving clear to almost clear grade after treatment with E-BPO 5% cream were: about 11.35% (week 2), about 25.75% (week 4), about 41.8% (week 8) and about 46.8% (week 12). In comparison, the corresponding mean percentage of patients achieving clear to almost clear grade after treatment with the vehicle cream were: about 4.3% (week 2), about 10.3% (week 4), about 20.9% (week 8) and about 21% (week 12).

As seen from these results, topical application of BPO is highly effective as a first-line treatment of rosacea, including up to about 50% of patients achieving a clear to almost clear grade after 12 weeks of treatment with 5% E-BPO cream, which is significantly greater than the effect observed after treatment with vehicle cream.

TABLE 1A

Improvement in IGA

| | IGA | | Difference | | Weekly Change | |
|---|---|---|---|---|---|---|
| Week | Drug 01 | Vehicle 01 | (Drug − Vehicle) | P-Value | Drug | Vehicle |
| 2 | 9.50 | 3.10 | 6.40 | 0.009 | 9.50 | 3.10 |
| 4 | 25.40 | 6.50 | 18.90 | <0.001 | 15.90 | 3.40 |
| 8 | 39.60 | 15.80 | 23.80 | <0.001 | 14.20 | 9.30 |
| 12 | 43.50 | 16.10 | 27.40 | <0.001 | 3.90 | 0.30 |

TABLE 1B

Improvement in the IGA

| | IGA | | Difference | | Weekly Change | |
|---|---|---|---|---|---|---|
| Week | Drug 02 | Vehicle 02 | (Drug − Vehicle) | P-Value | Drug | Vehicle |
| 2 | 13.20 | 5.50 | 7.70 | 0.017 | 13.20 | 5.50 |
| 4 | 26.10 | 14.10 | 12.00 | 0.009 | 12.90 | 8.60 |
| 8 | 44.00 | 26.00 | 18.00 | 0.006 | 17.90 | 11.90 |
| 12 | 50.10 | 25.90 | 24.20 | <0.001 | 6.10 | −0.10 |

Secondary Efficacy Analyses:
The proportions of subjects with a secondary measure of success (defined as change in the mean inflammatory lesion count from Baseline to Weeks 2, 4, 8 and 12) are shown in Tables 2A, 2B, 3A and 3B, and FIGS. 2 and 3.

The mean percentage improvement values of E-BPO 5% cream were: about 42.5% (week 2), about 58% (week 4), about 68% (week 8) and about 69% (week 12). In comparison, the mean percentage improvement values of the vehicle cream were: about 24% (week 2), about 36% (week 4), about 42.6% (week 8) and about 42.4% (week 12).

As seen from these results, topical application of BPO is highly effective as a first-line treatment of rosacea, including over 69% decrease in inflammatory lesions after at least 12 weeks of treatment, which is more than 1.5× the effect observed after treatment with vehicle cream.

TABLE 2A

Percent change in inflammatory lesion count

| Week | % Change in Lesion Count | | Difference | Weekly Change | |
|---|---|---|---|---|---|
| | Drug 01 | Vehicle 01 | (Drug-Vehicle) | Drug | Vehicle |
| 2 | −41.34 | −22.85 | −18.49 | −41.34 | −22.85 |
| 4 | −58.31 | −35.40 | −22.91 | −16.97 | −12.55 |
| 8 | −66.94 | −41.74 | −25.20 | −8.63 | −6.34 |
| 12 | −68.20 | −38.78 | −29.42 | −1.26 | 2.96 |

TABLE 2B

Percent change in inflammatory lesion count

| Week | % Change in Lesion Count | | Difference | Weekly Change | |
|---|---|---|---|---|---|
| | Drug 02 | Vehicle 02 | (Drug-Vehicle) | Drug | Vehicle |
| 2 | −43.69 | −25.36 | −18.33 | −43.69 | −25.36 |
| 4 | −57.98 | −37.25 | −20.73 | −14.29 | −11.89 |
| 8 | −68.74 | −43.46 | −25.28 | −10.76 | −6.21 |
| 12 | −69.40 | −46.00 | −23.40 | −0.66 | −2.54 |

The absolute reduction in inflammatory lesion count also demonstrates the enhanced efficacy of using BPO as a first-line treatment for rosacea. As seen from the results in Tables 3A and 3B, and illustrated in FIG. 3, topical application of 5% BPO is highly effective as a first-line treatment of rosacea, decreasing the absolute lesion count by at least 1.5× the decrease observed after treatment with vehicle cream.

TABLE 3A

Absolute change in inflammatory lesion count

| Week | Lesion Count (number) | | Difference (Drug − Vehicle) | P-Value | Weekly Change | |
|---|---|---|---|---|---|---|
| | Drug 01 | Vehicle 01 | | | Drug | Vehicle |
| 2 | −10.50 | −5.50 | −5.00 | <0.001 | −10.50 | −5.50 |
| 4 | −14.60 | −8.70 | −5.90 | <0.001 | −4.10 | −3.20 |
| 8 | −16.80 | −10.60 | −6.20 | <0.001 | −2.20 | −1.90 |
| 12 | −17.40 | −9.50 | −7.90 | <0.001 | −0.60 | 1.10 |

TABLE 3B

Absolute change in inflammatory lesion count

| Week | Lesion Count (number) | | Difference (Drug − Vehicle) | P-Value | Weekly Change | |
|---|---|---|---|---|---|---|
| | Drug 02 | Vehicle 02 | | | Drug | Vehicle |
| 2 | −13.00 | −8.00 | −5.00 | <0.001 | −13.00 | −8.00 |
| 4 | −16.70 | −10.50 | −6.20 | <0.001 | −3.70 | −2.50 |
| 8 | −20.00 | −12.40 | −7.60 | <0.001 | −3.30 | −1.90 |
| 12 | −20.30 | −13.30 | −7.00 | <0.001 | −0.30 | −0.90 |

Figure 2:
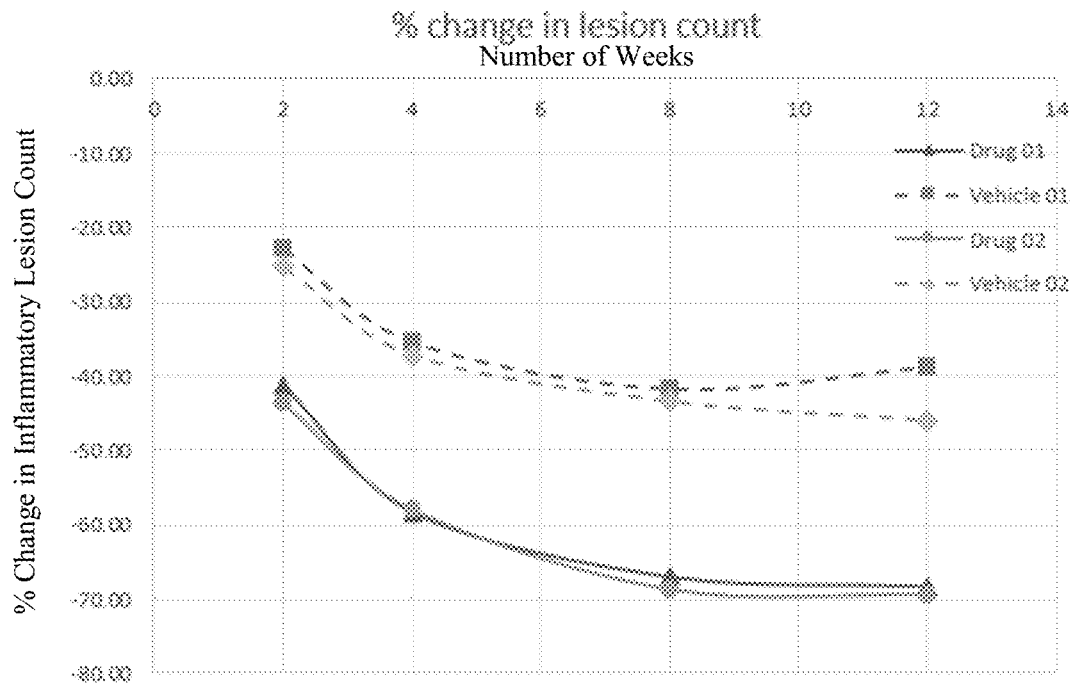
FIG. 2 is a graph presenting the percentage decrease in inflammatory lesion count per time of administering BPO composition as compared with vehicle alone over a period of time of 12 weeks.
Figure 3:
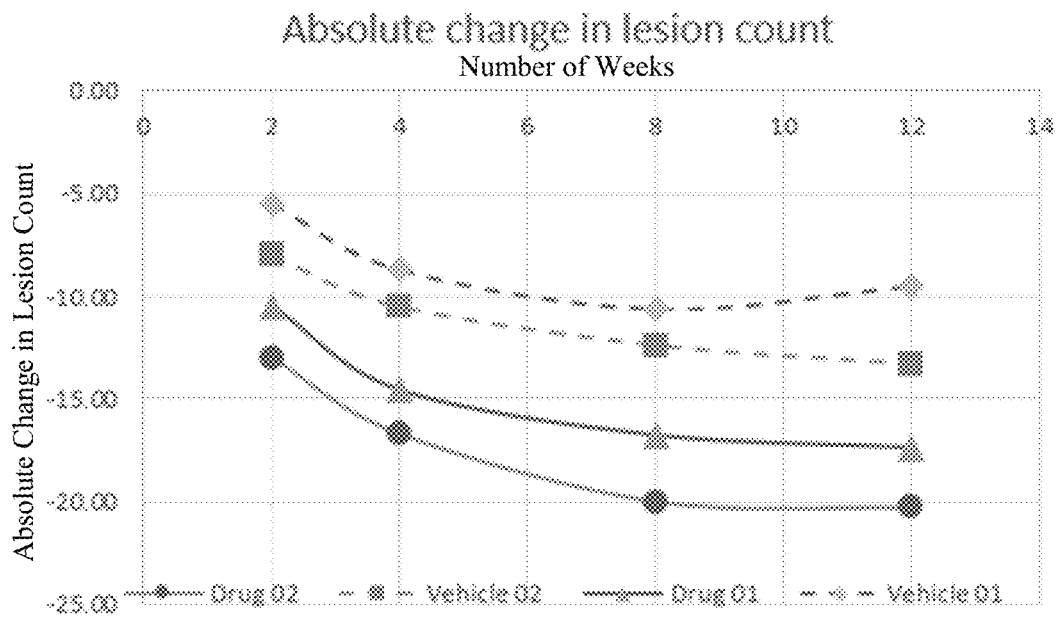
FIG. 3 is a graph presenting the absolute decrease in inflammatory lesion count per time of administering BPO composition as compared with vehicle alone over a period of time of 12 weeks.

Early Onset of Action:

The results in Tables 1A to 3B and FIGS. 1 to 3 also demonstrate the early onset of action in the BPO-treatment of rosacea. For example, as shown in Tables 2A and 2B, on average, an about 40% decrease in inflammatory lesions is observed after only 2 weeks of treatment compared to less than about 25% decrease in inflammatory lesions in the same time period after treatment with vehicle. Early onset is also demonstrated by over about 58% decrease in inflammatory lesions in 4 weeks, and almost about 70% decrease in inflammatory lesions in 8 weeks, compared to only about 40% decrease in weeks 4 and 8 with vehicle cream treatment. Surprisingly, the effect achieved after 8 weeks of treatment is comparable to the effect achieved after 12 weeks of treatment indicating an onset response at an early point in time during the treatment schedule, and reaching a plateau after 8 weeks of treatment. Similar results are observed for IGA and absolute change in lesion count in Tables 1A, 1B, 3A and 3B. That is, surprisingly, the highest effects were observed after 2 weeks of treatment, and the difference in the changes observed after 8 weeks and after 12 weeks of treatment was negligible.

Recently, clinical studies on topical treatment of inflammatory lesions of rosacea using 1% ivermectin cream have been submitted to FDA for approval of the Galderma product SOOLANTRA® (available at https://www.accessdata.fda.gov/drugsatfda_docs/nda/2014/206255Orig1s000StatR.pdf, last accessed Jul. 4, 2019). The results after 2 weeks and 8 weeks of treatment with SOOLANTRA® available at Section 3.2.7 of this study are reproduced below. The "time to onset" of efficacy was determined using a conditional backward stepwise testing approach of the co-primary efficacy endpoints for the different weeks (Weeks 12, 8, 4 and 2). As shown in Table 13 of the SOOLANTRA® study, reproduced below, SOOLANTRA® was statistically superior ($\alpha=0.05$) to vehicle on the co-primary endpoints starting from Week 4. That is, the fastest onset results in the SOOLANTRA® clinical study having statistical significance ($\alpha<0.05$) were observed after 4 weeks of treatment by a 10% success in IGA.

TABLE 13

| | Results for the Co-Primary Efficacy Endpoints over Time (ITT.LOCF) | | | | | |
|---|---|---|---|---|---|---|
| | IGA Success[1]; n (%) | | | Absolute Change in Inflammatory Lesion Counts: Mean (SD) | | |
| | SOOLANTRA | Vehicle | P-value[2] | SOOLANTRA | Vehicle | P-value[3] |
| Study 18170 | N = 451 | N = 232 | | N = 451 | N = 232 | |
| Week 12 | 173 (38.4%) | 27 (11.6%) | <0.001 | 20.5 (16.0) | 12.0 (13.5) | <0.001 |
| Week 8 | 104 (23.1%) | 23 (9.9%) | <0.001 | 17.9 (14.8) | 10.1 (14.0) | <0.001 |
| Week 4 | 49 (10.9%) | 13 (6.6%) | 0.021 | 13.6 (14.9) | 7.7 (12.3) | <0.001 |
| Week 2 | 17 (3.8%) | 5 (2.2%) | 0.267 | 8.8 (13.4) | 5.1 (11.1) | <0.001 |
| Study 18171 | N = 459 | N = 229 | | N = 459 | N = 229 | |
| Week 12 | 184 (40.1%) | 43 (18.8%) | <0.001 | 22.2 (14.9) | 13.4 (14.5) | <0.001 |
| Week 8 | 126 (27.5%) | 28 (12.2%) | <0.001 | 19.8 (14.4) | 11.2 (13.3) | <0.001 |
| Week 4 | 54 (11.8%) | 13 (5.7%) | 0.014 | 14.3 (13.8) | 7.8 (11.9) | <0.001 |
| Week 2 | 16 (3.5%) | 6 (2.6%) | 0.551 | 9.1 (12.3) | 6.3 (11.7) | 0.006 |

Source Reviewer's Analysis
[1]Success is defined as achieving an IGA score of 0 (Clear) or 1 (Almost Clear).
[2]P-value calculated from a CMH test certified by analysis centers.
[3]P-value calculated based on an ANCOVA model with baseline lesion count, treatment, and analysis centers as factors.

Figure 4:
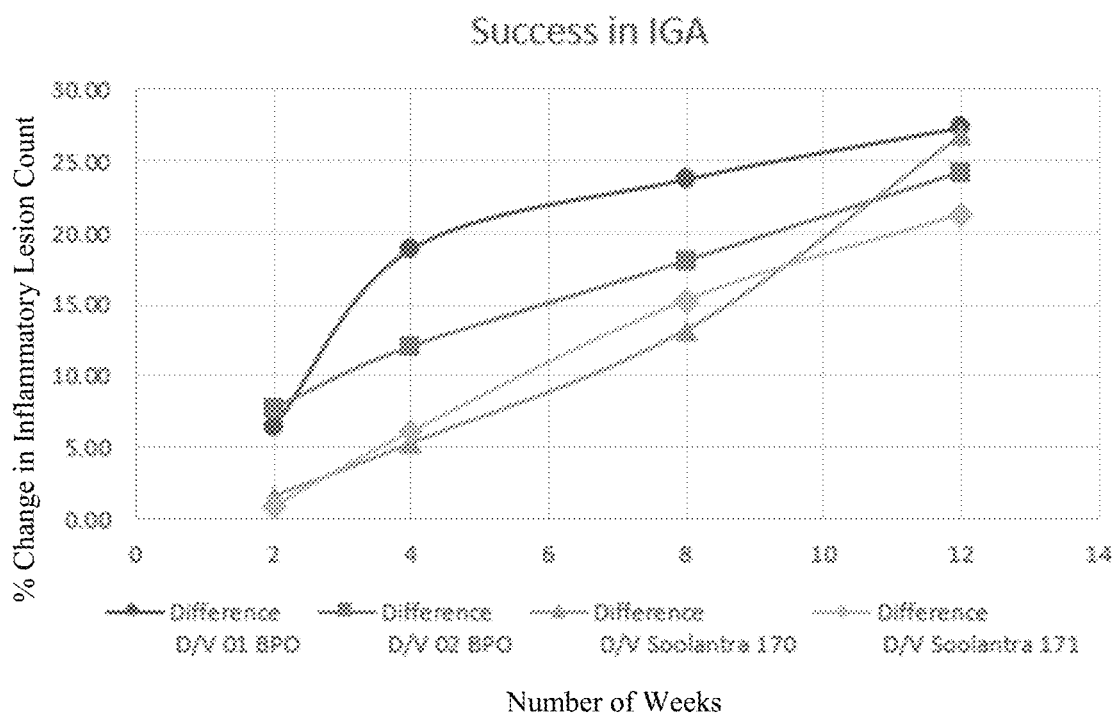
FIG. 4 is a graph presenting the difference in drug and vehicle IGA per time of administering BPO composition according to exemplary embodiments of this application as compared with the difference in drug and vehicle IGA per time of administering SOOLANTRA®.

In comparison, and quite surprisingly, in the BPO-based treatment of rosacea, as described in the subject application, the fastest onset success was obtained by about 25% success in IGA after only 4 weeks of treatment, which is more than twice the effect observed after treatment with SOOLANTRA® for four weeks. In fact, fastest onset success can be achieved even earlier, as shown by an about 10% success in IGA after 2 weeks of BPO-treatment. The difference in the results achieved using the two treatment methods is shown in FIG. 4.

Data shown in Tables 1A, 1B, 2A, 2B, 3A and 3B also include the corresponding P-Values. The P-value is a statistical calculation of the difference between the drug and the vehicle (placebo). A P-Value <0.05 indicates statistical superiority of the drug over the vehicle. In order for a drug to be approved, the P-Value at week 12 must be <0.05. Surprisingly, as shown in the tables of this application, the P-Values <0.05 at all timepoints—2 weeks, 4 weeks, 8 weeks and 12 weeks. The P-values from the clinical studies of BPO-based treatment of rosacea, as described in this application, is another, surprising indication of the fast onset activity of the method described herein.

The results in the subject application indicate that BPO-treatment of rosacea should be recommended as the first line treatment of rosacea, contrary to known methods of using BPO in combination with other active agents or using BPO as only a second-line or even later-stage treatment. Moreover, such early onset of action can improve patient compliance to treatment protocols, resulting in an even higher percentage of success.

Subcutaneous Reaction: BPO is a strong oxidizer, and would be expected to result in a significant increase in subcutaneous reaction, such as dryness, scaling, itching, burning and stinging, in patients being treated for rosacea with a BPO-containing formulation. As demonstrated in U.S. Application Publication Nos. 2010/0016443, 2017/0281571 and 2018/0147165 and U.S. Pat. No. 9,687,465, encapsulation of BPO can reduce the irritation associated with BPO. Thus, resulting in only a minor increase in subcutaneous reactions compared to the use of un-encapsulated BPO. Surprisingly, however, following the use of BPO in the studies described herein, the number of rosacea patients reporting no and/or almost no subcutaneous reactions increased as the use of the drug continued. Moreover, the percentage of patients using the drug reporting no subcutaneous reactions was comparable, and for some conditions, surprisingly, higher than the percentage of patients using the vehicle. That is, the treatment regimen described herein has an adverse events value similar to, or in some instances, surprisingly, even less than, the adverse events value of a vehicle control.

Table 4A and 4B list the percentage of patients reporting no subcutaneous reactions at 2, 4, 8 and 12 weeks compared to the percentage of patients reporting no subcutaneous reaction at baseline.

TABLE 4A

| | Percentage of Patients Reporting No Subcutaneous Reactions | | | | | | | |
|---|---|---|---|---|---|---|---|---|
| | Dryness | | Scaling | | Itching | | Burning/Stinging | |
| Week | Drug 01 | Vehicle 01 | Drug 01 | Vehicle 01 | Drug 01 | Vehicle 01 | Drug 01 | Vehicle 01 |
| Baseline | 45.6 | 46.0 | 66.5 | 68.1 | 35.6 | 41.6 | 52.7 | 49.6 |
| 2 | 61.4 | 58.6 | 76.7 | 68.5 | 51.7 | 55.0 | 56.8 | 52.7 |
| 4 | 64.4 | 58.2 | 83.1 | 76.4 | 63.1 | 59.1 | 67.8 | 63.6 |
| 8 | 71.1 | 58.9 | 83.3 | 72.9 | 69.7 | 61.7 | 75.0 | 69.2 |
| 12 | 71.5 | 65.4 | 84.2 | 72.9 | 68.8 | 52.3 | 74.2 | 70.1 |

TABLE 4B

Percentage of Patients Reporting No Subcutaneous Reactions

| Week | Dryness | | Scaling | | Itching | | Burning/Stinging | |
|---|---|---|---|---|---|---|---|---|
| | Drug 02 | Vehicle 02 | Drug 02 | Vehicle 02 | Drug 02 | Vehicle 02 | Drug 02 | Vehicle 02 |
| Baseline | 48.4 | 48.8 | 66.1 | 66.1 | 47.6 | 52.9 | 64.1 | 71.9 |
| 2 | 55.1 | 65.8 | 78.2 | 82.5 | 60.5 | 65.0 | 63.8 | 70.8 |
| 4 | 56.8 | 64.7 | 81.3 | 80.7 | 63.5 | 65.5 | 75.1 | 79.8 |
| 8 | 63.1 | 63.5 | 85.4 | 81.7 | 71.2 | 69.6 | 77.7 | 80.0 |
| 12 | 64.8 | 62.3 | 82.8 | 81.6 | 71.2 | 71.9 | 78.5 | 78.9 |

Although the exemplary embodiments of the present disclosure have been described in detail with reference to the accompanying examples and drawings, the present disclosure is not limited thereto and can be embodied in many different forms without departing from the technical concept of the present disclosure. Therefore, the exemplary embodiments of the present disclosure are provided for illustrative purposes only and are not intended to limit the technical concept of the present disclosure. The protective scope of the present disclosure should be construed based on any appended claims and combinations thereof, and all the technical concepts in the equivalent scope thereof should be construed as falling within the scope of the present disclosure. As various changes could be made in the above methods and compositions without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the exemplary embodiments disclosed herein. It is intended that the specification be considered exemplary only, with the scope and spirit of the described subject matter being indicated by the claims.

What is claimed is:

1. A treatment regimen for providing early onset of action in the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein said pharmaceutical composition is a cream or an emulsion, wherein a primary measure of success in a group of subjects is at least about 9% to about 40%, and wherein the primary measure of success is defined as a 2-grade improvement in Investigator Global Assessment (IGA) and clear or almost clear, wherein the primary measure of success is at least about 9% after about 2 weeks,
   wherein the benzoyl peroxide is the sole active ingredient administered to the subject in need of said treatment during the duration of the regimen,
   wherein the benzoyl peroxide is encapsulated and/or microencapsulated, and
   wherein the treatment regimen provides early onset of action in the therapeutic treatment of rosacea.

2. The treatment regimen of claim 1, wherein the primary measure of success is at least about 25% after about 4 weeks.

3. The treatment regimen of claim 1, wherein the primary measure of success is at least about 40% after about 8 weeks.

4. The treatment regimen of claim 1, wherein the pharmaceutical composition comprises about 5% w/w of benzoyl peroxide.

5. The treatment regimen of claim 1, wherein the regimen is a first-line therapy for the treatment of rosacea.

6. The treatment regimen of claim 1, wherein the rosacea is any of erythematotelengietatic, papulopustular, phymatous or ocular rosacea.

7. The treatment regimen of claim 1, wherein said pharmaceutical composition is an extended release formulation.

8. The treatment regimen of claim 1, wherein said regimen has adverse events values similar to or lower than the adverse events values of a vehicle control.

9. A treatment regimen for providing early onset of action in the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of at least about 2, 4, 8 or 12 weeks, wherein said pharmaceutical composition is a cream or an emulsion, wherein a secondary measure of success in a group of such subjects is at least about 40% to at least about 65%, and wherein the secondary measure of success is defined as mean inflammatory lesion count percent reduction from baseline, wherein the secondary measure of success is at least about 40% after at least about 2 weeks,
   wherein the benzoyl peroxide is the sole active ingredient administered to the subject in need of said treatment during the duration of the treatment regimen,
   wherein the benzoyl peroxide is encapsulated and/or microencapsulated, and
   wherein the treatment regimen provides early onset of action in the therapeutic treatment of rosacea.

10. The treatment regimen of claim 9, wherein the secondary measure of success is at least about 55% after at least about 4 weeks.

11. The treatment regimen of claim 9, wherein the secondary measure of success is at least about 65% after at least about 8 weeks.

12. The treatment regimen of claim 9, wherein the pharmaceutical composition comprises about 5% w/w of benzoyl peroxide.

13. The treatment regimen of claim 9, wherein the regimen is a first-line therapy for the treatment of rosacea.

14. The treatment regimen of claim 9, wherein the rosacea is any of erythematotelengietatic, papulopustular, phymatous or ocular rosacea.

15. The treatment regimen of claim 9, wherein said pharmaceutical composition is an extended release formulation.

16. The treatment regimen of claim 9, wherein said regimen has adverse events values similar to or lower than the adverse events values of a vehicle control.

17. A treatment regimen for providing early onset of action in the therapeutic treatment of rosacea, the regimen comprising topically applying to the skin of a subject in need of said treatment a pharmaceutical composition, the pharmaceutical composition comprising about 2.5% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is a cream or an emulsion, wherein said pharmaceutical composition is applied once daily for a period of at least about 2, 4, 8 or 12 weeks, and wherein the absolute reduction in lesion count after about 2 weeks is at least twice the absolute reduction in lesion count after about 4 weeks of treatment,
- wherein the benzoyl peroxide is the sole active ingredient administered to the subject in need of said treatment during the duration of the treatment regimen,
- wherein the benzoyl peroxide is encapsulated and/or microencapsulated, and
- wherein the treatment regimen provides early onset of action in the therapeutic treatment of rosacea.

18. The treatment regimen of claim 17, wherein the pharmaceutical composition comprises about 5% w/w of benzoyl peroxide.

19. The treatment regimen of claim 17, wherein the regimen is a first line therapy for the treatment of rosacea.

20. The treatment regimen of claim 17, wherein the rosacea is any of erythematotelengietatic, papulopustular, phymatous or ocular rosacea.

21. The treatment regimen of claim 17, wherein said pharmaceutical composition is an extended release formulation.

22. The treatment regimen of claim 17, wherein said regimen has an adverse events values similar to or lower than the adverse events values of a vehicle control.

23. The treatment regimen of claim 17, wherein a primary measure of success in the group of subjects is at least about 9% to about 40%, and wherein the primary measure of success is defined as a 2-grade improvement in Investigator Global Assessment (IGA) and clear or almost clear.

24. The treatment regimen of claim 17, wherein a secondary measure of success in the group of subjects is at least about 40% to at least about 65%, and wherein the secondary measure of success is defined as mean inflammatory lesion count percent reduction from baseline.

* * * * *